United States Patent
Bandyopadhyay et al.

[11] Patent Number: 5,178,004
[45] Date of Patent: Jan. 12, 1993

[54] REFLECTION TYPE SKIN FRICTION METER

[75] Inventors: Promode R. Bandyopadhyay; Leonard M. Weinstein, both of Newport News, Va.

[73] Assignee: The United States of America as represented by the Administrator of the National Aeronautics and Space Administration, Washington, D.C.

[21] Appl. No.: 742,238

[22] Filed: Aug. 8, 1991

[51] Int. Cl.5 ............................................. G01M 9/00
[52] U.S. Cl. ........................................... 73/147; 73/9
[58] Field of Search ............... 73/9, 10, 147; 356/357, 356/372

[56] References Cited

U.S. PATENT DOCUMENTS

| | | | |
|---|---|---|---|
| 2,935,870 | 5/1960 | Lyons, Jr. ............................ | 73/147 |
| 3,596,513 | 8/1971 | Sandstedt . | |
| 3,623,361 | 11/1969 | Funk, Jr. . | |
| 3,714,824 | 2/1973 | Bush . | |
| 4,377,343 | 3/1983 | Monson . | |
| 4,836,035 | 6/1989 | Tcheng et al. ....................... | 73/147 |

OTHER PUBLICATIONS

L. H. Tanner, "A skin friction meter, using the viscosity balance principle, suitable for use with flat or curved metal surfaces." *J. of Physics E: Scientific Instruments*, vol. 10, (printed in Great Britain), 1977, pp. 278–284.

Weinstein, L. M. and Bandyopadhyay, P. R. "A Simplified Oil-Film Skin-Friction Meter", First National Fluid Dynamics Congress, Cincinnati, Ohio, Jul. 25-28, 1988, (AIAA/ASME/SIAM/APS).

Seto, J. and Hornung, H. G., "Internally Mounted Thin-Liquid-Film Skin-Friction Meter—Comparison with Floating Element Method With and Without Pressure Gradient", *AIAA* 91-0060, CA Institute of Technology, Pasadena, Calif., 29th Aerospace Sciences Meeting, Reno, Nev. Jan. 7-10, 1991.

*Primary Examiner*—Robert Raevis
*Attorney, Agent, or Firm*—Kevin B. Osborne

[57] ABSTRACT

A housing block is provided having an upper surface conforming to the test surface of a model or aircraft. An oil film is supplied upstream of a transparent wedge window located in this upper surface by an oil pump system located external to the housing block. A light source located within the housing block supplies a light beam which passes through this transparent window and is reflected back through the transparent window by the upper surface of the oil film to a photo-sensitive position sensor located within the housing. This position sensor allows the slope history of the oil film caused by an aerodynamic flow to be determined. The skin friction is determined from this slope history. Internally located mirrors augment and sensitize the reflected beam as necessary before reaching the position sensor. In addition, a filter may be provided before this sensor to filter the beam.

18 Claims, 2 Drawing Sheets

REFLECTION TYPE SKIN FRICTION METER

ORIGIN OF THE INVENTION

The invention described herein was made jointly in the performance of work under a NASA Contract and an employee of the United States Government. In accordance with 35 U.S.C. 202, the contractor elected not to retain title.

BACKGROUND OF THE INVENTION

1. Technical Field of the Invention

The present invention relates generally to skin friction meters and more particularly to a reflection type skin friction meter for both flight and wind tunnel applications.

2. Discussion of the Related Art

The determination of skin friction is very important in fluid mechanical studies or aerodynamic effects. Several methods have been disclosed and include a dual beam interferometer disclosed in U.S. Pat. No. 4,377,343 to Monson. In this patent, each beam is read by a light detector to measure the thickness of an applied oil film at two different points in order to generate a thickness history indication of skin friction by counting the number of interference fringes. A clean, particle free flow is required since the presence of, e.g., a dust speck in the oil film can disrupt the required continuous counting. Also, this method is very sensitive to vibration, requires a relatively large laser capable of producing coherent light in order to obtain good interference fringes, is not easily adaptable from wind tunnel test to flight conditions, requires an optically smooth surface for the interferometer, and has a complicated optical system to produce the necessary two beams.

Another proposal for measuring skin friction is disclosed in U.S. Pat. No. 3,714,824 to Bush. A ring shaped element is placed in a seat in an upright container and subjected to an air flow. The frictional forces of the flow will overcome gravity and lift the ring off its seat at a point corresponding to the specific skin friction. This method only permits the determination of large area surface averaged skin friction of a particular ring mounted only vertically, precluding straightforward adaption to a variety of surfaces and/or velocities. Also, the method cannot be adapted to flight conditions.

OBJECTS OF THE INVENTION

It is accordingly an object of the present invention to measure the skin friction in a small area on an aerodynamic surface by obtaining the oil film slope history.

It is another object of the present invention to obtain these measurements without undue concern for particles in the flow.

It is a further object of the present invention to obtain these measurements without the need for a coherent beam of light provided by large lasers.

It is yet another object of the present invention to obtain these measurements both in wind tunnel test conditions and in flight.

It is a further object of the present invention to obtain these measurements without the need for an optically smooth surface.

It is a further object of the present invention to obtain these measurements simply without the need for a complicated optical system.

It is yet another object of the present invention to obtain these measurements for a wide variety of surfaces and flow velocities.

Additional objects and advantages of the present invention are apparent from the drawings and specification which follow.

SUMMARY OF THE INVENTION

The foregoing and additional objects are obtained by a skin friction meter according to the present invention. A housing block is provided having an upper surface conforming to the test surface of a model or aircraft. An oil film is supplied to a transparent window located in this upper surface by an oil pump system located external to the housing block. A light source located within the housing block supplies a light beam which passes through this transparent window and is reflected back through the transparent window by the upper surface of the oil to a photo-sensitive position sensor located within the housing. This position sensor allows the slope history of the oil film caused by an aerodynamic flow to be determined. The skin friction is then determined from this slope history. Internally located mirrors increase the optical path and thus increase the angle deflection sensitivity as necessary before reaching the position sensor. In addition, a filter may be provided before this sensor to reject stray light.

DESCRIPTION OF THE PREFERRED EMBODIMENTS

Figure 1:
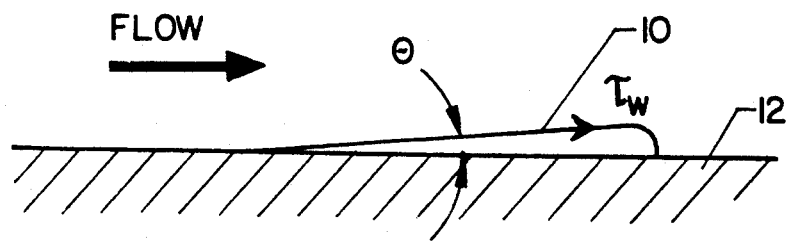
FIG. 1 is a schematic representation of the oil film flow, on a surface, caused by moving air.
Figure 2:
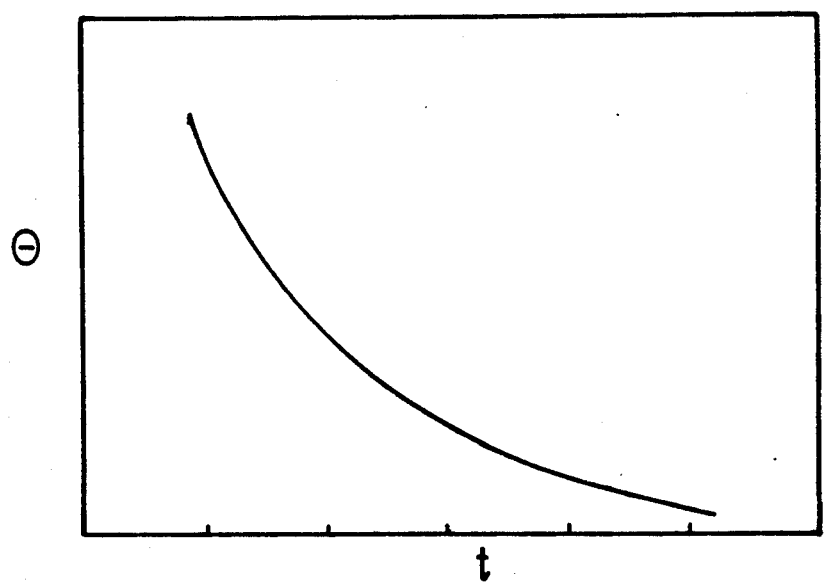
FIG. 2 is a graph of the oil film slope history.

Referring to FIG. 1, lubrication theory is applied to study the dynamics of a thin, two-dimensional oil film 10 in contact with a solid aerodynamic surface 12 and lying under an aerodynamic boundry layer flow. The oil film shape develops primarily under the action of three forces, namely skin friction, gravity and pressure gradient. For a film having a small thickness compared to its length and width, the latter two forces are small. In addition, surface tension is negligible except at the leading edge of the oil film. The wall-shear stress at the airforce interface $\tau_w$ is defined as $$\tau_w = \mu/(\theta t) \qquad (1)$$

where t is time, $\theta$ is the oil film slope at time t, and $\mu$ is the oil viscosity. When the oil film is thin, i.e., is measured in nanometers, it sticks to the surface in most situations so that the fluid surface has negligible velocities compared to the air located a very short distance above. Accordingly, the determined $\tau_w$ at the air-oil interface is equivalent to the wall-shear stress of the boundry layer. Assuming that the oil viscosity is known, this wall stress can be determined by measuring the oil slope time history, and using this to determine $\theta$ and t from the best fit to a rectangular hyperbola. This curve is shown in FIG. 2.

Figure 3:
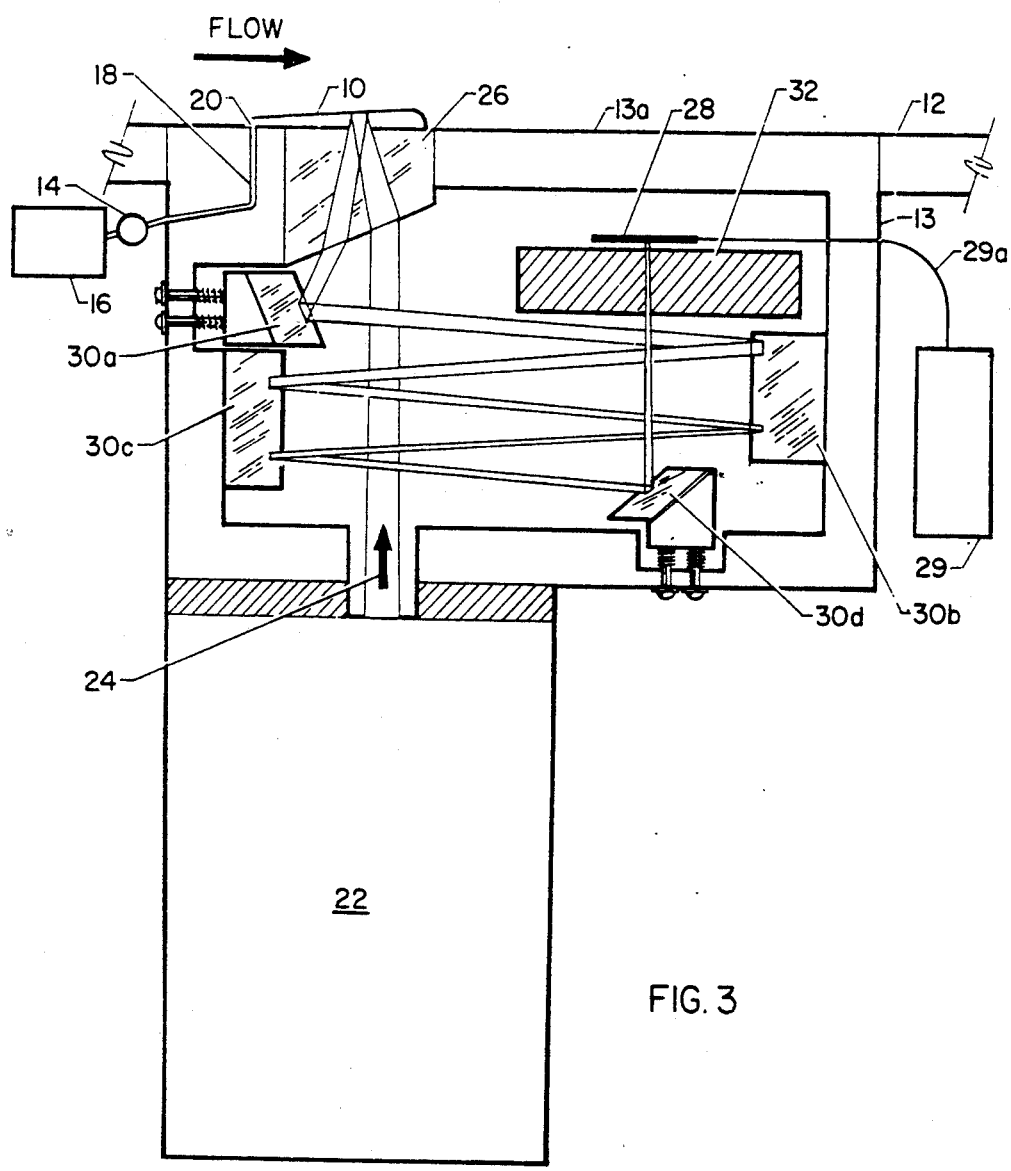
FIG. 3 is a schematic of an internal reflection type skin friction meter according to the present invention.

Referring to FIGS. 1 and 3, an oil film 10 is applied to an aerodynamic outer solid surface of a model or aircraft 12 which is subjected to an aerodynamic flow such as air or other gases. An internal housing block 13 is provided within the model or aircraft and has an upper surface 13a conforming with surface of the model or aircraft 12. Oil of known viscosity $\mu$ is supplied to housing upper surface 13a by an on-demand external pump 14 from external reservoir 16, through conduit 18, and to spanwise slot or port 20 in housing upper surface 13a. Port 20 is located upstream, e.g., one cm upstream, of the location where the skin friction stress $\tau_w$ is to be measured. Oil supply component 18 is located within housing 13. Pump 14 and reservoir 16 are usually separate and external to housing 13.

The internal reflection type oil film skin friction meter is also located within housing 13. A light source 22 such as a solid state diode laser or small filament tungsten light with focusing lens is provided to supply a light beam 24 through an inner side of a transparent wedge window 26 fitted into an aperture in aerodynamic surface 13a such that the oil film is located above the window having an outer side located flush with the surface. Since the light beam need not be coherent, a diode laser or small filament tungsten light with focusing lens may be used rather than a larger, coherent light producing laser. Transparent wedge window 26 may be composed of any suitable transparent material such as transparent plastic. The window 26 may also have a relatively small, circular shape of, e.g., 10 mm in diameter. A wedge window is used to avoid multiple reflections. Light beam 24 passes through transparent window 26 and is reflected internally by the upper or outer surface of oil film 10 at an oil film aerodynamic flow interface and returned via transparent window 26 to a photo diode position sensor 28. This sensor determines the location of the center of the intensity of the beam of light reaching it. As the slope of oil film 10 changes with time, the location of the returned beam 24 on position sensor 28 also changes. The output voltage of position sensor 28 is processed and stored in an external and separate electronic circuit 29 connected by wiring 29a, for subsequent processing and display of the skin friction value $\tau_w$ computed by known methods from $\tau_w = \mu/\theta t$, where $\mu$ is the viscosity and $\theta t$ is the slope history. A cascade of reflecting mirrors 30a, 30b, 30c and 30d may be employed to augment the length of the returned light beam 24 and to improve the sensitivity of the sensed beam location. For example, the total reflected length of beam 24 may be approximately six and one-half inches. An optical filter 32 may also be employed to filter the beam before it reaches position sensor 28 in order to reduce the effect of or block stray light.

The provision of light source, mirrors and position sensor within housing block 13 allows these optical components to be rigidly mounted therein in a prealigned aligned manner prior to rigid installation of the housing block within within the model or aircraft. Accordingly, relative vibration between the optical components and the test model or aircraft outer surface can be avoided or eliminated. The entire housing is extremely compact and may fit within a palm. For example, a constructed embodiment of the housing has the following dimensions: $1 \times 1.5 \times 1.5$ inches, excluding the diode laser or compact tungsten lamp, and the oil reservoir, the pump, and output electronics.

The present invention is also relatively insensitive to particles or other contaminants in the oil originating from the airflow or oil itself, since the oil film slope history is smoothed for high frequency noise and low frequency local deviations from the mean rectangular hyperbola, and thus the smoothed curve can still give the correct skin friction even if part of the raw history is contaminated by dust in the oil. This provokes an advantage over interferometry which cannot give useful results when the continuity of any part of the time record is broken. Also, the present invention may be used to test a wide variety of surfaces which are hydrodynamically smooth but not necessarily optically smooth and which are exposed to airflows of various velocities in both test and in-flight environments.

Many modifications, improvements and substitutes will be apparent to one skilled in the art without departing from the spirit and scope of the present invention as described and shown in the specification and drawings, and as defined in the following claims.

What is claimed as new and desirable to be secured by Letters Patent is:

1. An apparatus for measuring the skin friction of an aerodynamic surface exposed to an aerodynamic flow, the apparatus comprising:
   a transparent window having an outer side located flush with the aerodynamic surface and an oppositely located inner side;
   means for supplying oil to the aerodynamic surface upstream of said transparent window, whereby an oil film having sloped outer surface id formed on the outer side of said transparent window by the aerodynamic flow;
   a light source for directing a light beam through the inner side of said transparent window and through the oil film, whereby the light beam is reflected by the sloped outer surface of the oil film at an aerodynamic flow interface back through said transparent window; and
   means for detecting the position of the reflected beam over a period of time, whereby a slope history of the oil film which is indicative of the skin friction of the aerodynamic surface is generated.

2. The skin friction measurements apparatus according to claim 1, wherein said light source is a diode laser.

3. The skin friction measurement apparatus according to claim 1, wherein said light source is a compact tungsten light with focusing lens.

4. The skin friction measurement apparatus according to claim 1, wherein said means for detecting the position of the reflected beam comprises a photodiode position sensor.

5. The skin friction measurement apparatus according to claim 1, further comprising reflecting mirrors arranged to reflect the reflected light beam prior to said means for detecting the position of the reflected beam, wherein the length of the beam is augmented.

6. The skin friction measurement apparatus according to claim 3, further comprising an optical filter for filtering the light beam before the bea reaches the photodiode position sensor to reduce the effect of stray light.

7. The skin friction measurement apparatus according to claim 1, wherein said transparent window is wedge shaped to prevent multiple reflections of the beam.

8. An internal apparatus for measuring the skin friction of an aerodynamic outer surface of a structure exposed to an aerodynamic flow, said apparatus comprising:
   a transparent window having an outer side located flush with the aerodynamic surface and an oppositely located inner side;
   means for supplying oil to the aerodynamic surface upstream of said transparent window, whereby an oil film having a sloped outer surface is formed on the outer side of said transparent window by the aerodynamic flow;

a light source for directing a light beam through the inner side of said transparent window and through the oil film, whereby the light beam is reflected by the sloped outer surface of the oil film at an on oil film-aerodynamic flow interface back through said transparent window;

means for detecting the position of the reflected beam over a period of time, whereby a slope history of the oil film which is indicative of the skin friction of the aerodynamic surface is generated; and a housing located within the structure, said housing enclosing said light source and continuous position detection means.

9. The internal skin friction measurement apparatus according to claim 8, wherein said light source is a diode laser.

10. The internal skin friction measurement apparatus according to claim 8, wherein said light source is a compact tungsten light with focusing lens.

11. The internal skin friction measurement apparatus according to claim 8, wherein said means for detecting the position of the reflected beam comprises a photodiode position sensor.

12. The internal skin friction measurement apparatus according to claim 11, further comprising an optical filter for filtering the light beam before the beam reaches the photodiode position sensor in order to block stray light.

13. The internal skin friction measurement apparatus according to claim 8, further comprising reflecting mirrors arranged within said housing to reflect the reflected light beam prior to said means for detecting the position of the reflected beam, wherein the length of the beam is augmented.

14. The internal skin friction measurement apparatus according to claim 8, wherein said transparent window is wedge shaped to prevent multiple reflections of the beam.

15. The internal skin friction apparatus according to claim 8, wherein said transparent window is located in an upper surface of said housing.

16. A method for determining the skin friction on an aerodynamic surface subjected to an aerodynamic flow, the method comprising the steps of:

providing a transparent window having an outer side flush with the aerodynamic surface and an oppositely located inner side;

applying oil of known viscosity to the surface upstream of the transparent window, whereby an oil film having a sloped outer surface is formed on the outer side of the transparent window by the aerodynamic flow;

directing a light beam through the inner side of said transparent window and into the slope oil film, whereby the light beam is reflected by the sloped outer surface of the oil film at an oil film-aerodynamic flow interface back through the oil film and the transparent window;

detecting the position of the reflected light over a period of time;

determining a slope of the oil film based on the detected position of reflected light; and determining the skin friction $\tau_w$ of the aerodynamic surface from the following relationship:

$$\tau_w = \mu/(\theta t),$$

wherein $\mu$ is the known viscosity of the applied oil, $\theta$ is slope of the oil film determine from the detected position of the reflected light, and t is the time of detection of the reflected light beam.

17. The method according to claim 16, further comprising optically filtering the reflected beam prior to said position detecting step to block stray light.

18. The method according to claim 16, further comprising augmenting the length of the reflected beam prior to said position detecting step.

* * * * *